US00PP37152P2

(12) United States Plant Patent
He et al.

(10) Patent No.: US PP37,152 P2
(45) Date of Patent: Dec. 16, 2025

(54) CHERRY PLUM TREE NAMED 'Farmer 6-10'

(50) Latin Name: *Prunus cerasifera*
Varietal Denomination: Farmer 6-10

(71) Applicant: Zhejiang Yangshengtang Institute of Natural Medication Co., Ltd, Zhejiang (CN)

(72) Inventors: Qiong He, Xinjiang (CN); Zhiqiang Bai, Xinjiang (CN); Xiaobo Cheng, Xinjiang (CN)

(73) Assignee: Zhejiang Yangshengtang Institute of Natural Medication Co., Ltd, Zhejiang (CN)

( * ) Notice: Subject to any disclaimer, the term of this patent is extended or adjusted under 35 U.S.C. 154(b) by 0 days.

(21) Appl. No.: 18/910,890

(22) Filed: Oct. 9, 2024

(51) Int. Cl.
*A01H 6/74* (2018.01)
*A01H 5/08* (2018.01)

(52) U.S. Cl.
USPC ..... Plt./184

(58) Field of Classification Search
USPC ..... Plt./184
CPC ..... A01H 6/7472; A01H 5/08
See application file for complete search history.

*Primary Examiner* — Keith O. Robinson
(74) *Attorney, Agent, or Firm* — Knobbe, Martens, Olson & Bear, LLP

(57) ABSTRACT

The new cherry plum variety 'Farmer 6-10' is characterized by having an open tree posture, and red colored, soft-textured fruits with yellow colored flesh.

3 Drawing Sheets

Latin name of the genus and species claimed: *Prunus cerasifera.*

Variety denomination: 'Farmer 6-10'.

BACKGROUND AND SUMMARY OF THE NEW VARIETY

This application relates to the discovery and asexual propagation of a new and distinct variety of cherry plum tree, *Prunus cerasifera 'Farmer* 6-10'. The new variety 'Farmer 6-10' was developed by using wild cherry plums found at an altitude of 1,100-1,600 m in Daxigou and Xiaoxigou, Huocheng County, Xinjiang, China, as parents. The new variety 'Farmer 6-10' resulted from sowing wild cherry plums and natural pollination. The new variety was selected and propagated through seedling breeding, high grafting propagation, and strain comparison experiments by Qiong He, Zhiqiang Bai and Xiaobo Cheng. The new variety 'Farmer 6-10' was asexually reproduced in Huocheng County, Yili, Xinjiang, China, by grafting.

The new variety 'Farmer 6-10' is characterized by having an open tree posture, and red colored, soft-textured fruits with yellow colored flesh.

The new variety 'Farmer 6-10' has red colored fruit skin compared to the black colored fruit skin for 'Farmer 7-07' (unpatented). Additionally, the fruit texture of the new variety 'Farmer 6-10' is soft, compared to the firm texture for 'Farmer 7-07'. Lastly, the new variety 'Farmer 6-10' has an oval-shaped stone, and it ripens mid-season, compared to the oblong-shaped stone and early ripening of 'Farmer 7-07'.

The detailed breeding process of 'Farmer 6-10' is described as follows:

In 1995, in Huocheng County, Yili, Xinjiang, wild cherry plum seeds were collected for sowing and breeding wild cherry plum live seedlings. After five years of repetitive investigation and comparison from 2002 to 2006, the single plants having stable traits, early fruiting, high productivity, high stress resistance, and good processing performance were screened, and in 2007, the scions of the screened single plants were collected and grafted onto 3-year-old bionic cultivated cherry plum trees through high grafting to obtain 'Farmer 6-10'.

BRIEF DESCRIPTION OF THE DRAWINGS

The accompanying color photographic illustrations were taken in Qingshuihe Town, Huocheng County, Xinjiang during the growing seasons of the cherry plum in 2021 and 2022. The colors are as nearly true as is reasonably possible in a color representation of this type.

DETAILED BOTANICAL DESCRIPTION OF THE VARIETY

Figure 1:
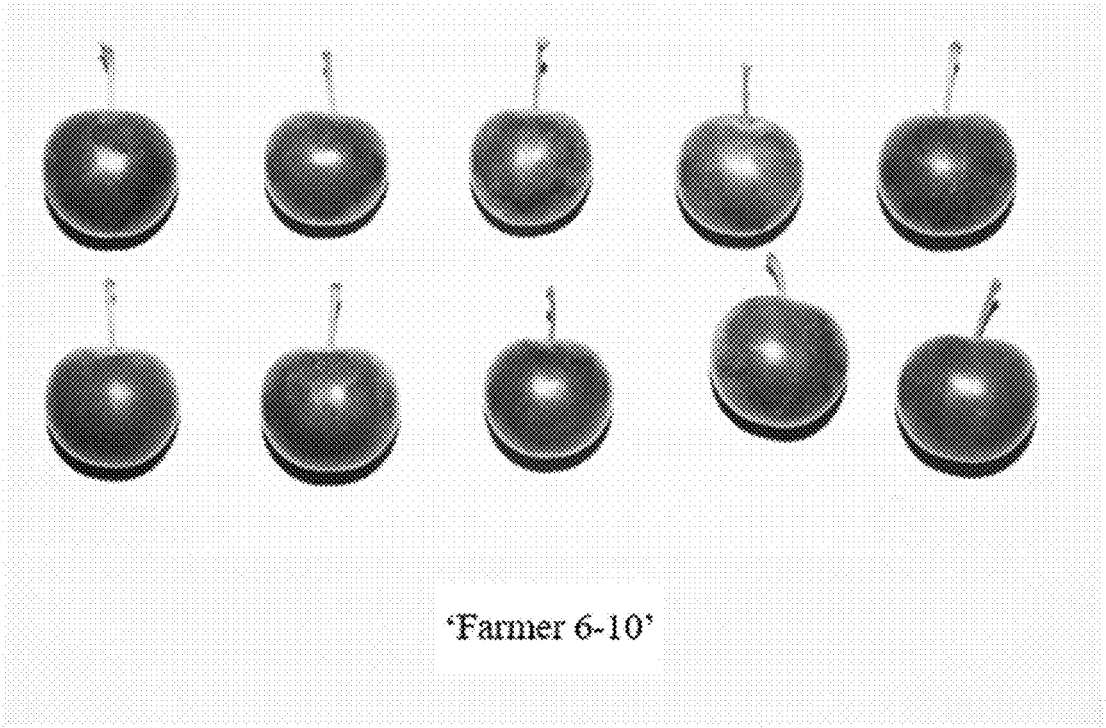
FIG. 1 shows the fruits of the new variety 'Farmer 6-10'.
Figure 2:
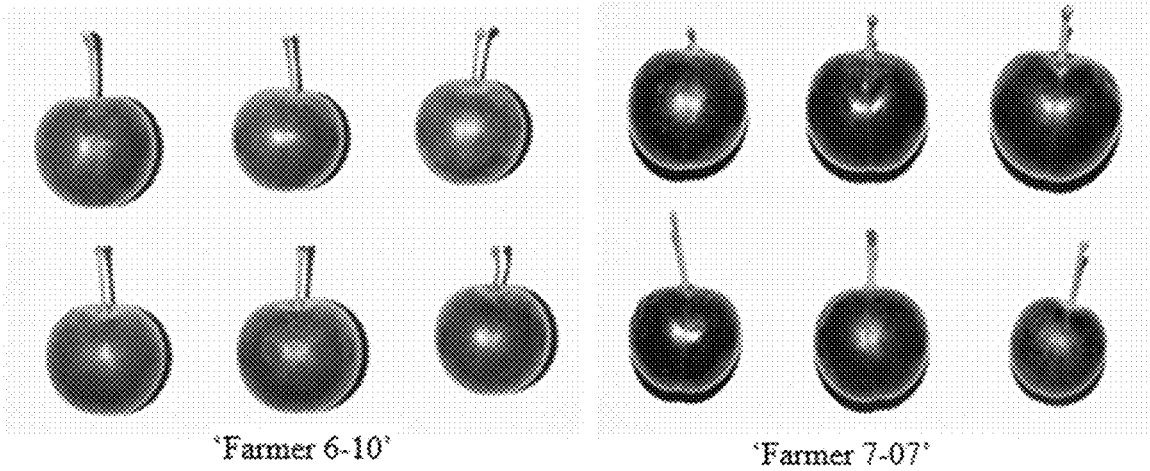
FIG. 2 shows the red colored fruits of the new variety 'Farmer 6-10', compared to the black colored fruits of 'Farmer 7-07'.
Figure 3:
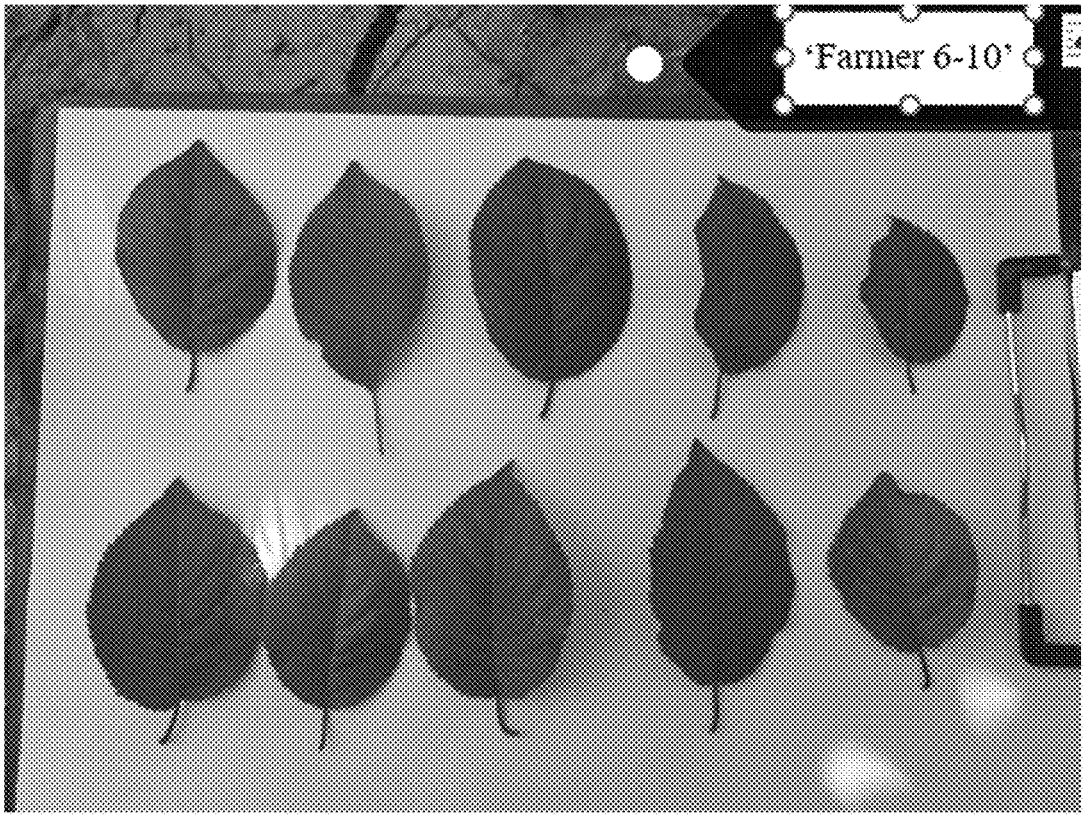
FIG. 3 shows typical specimens of foliage of the new variety 'Farmer 6-10'.
Figure 4:
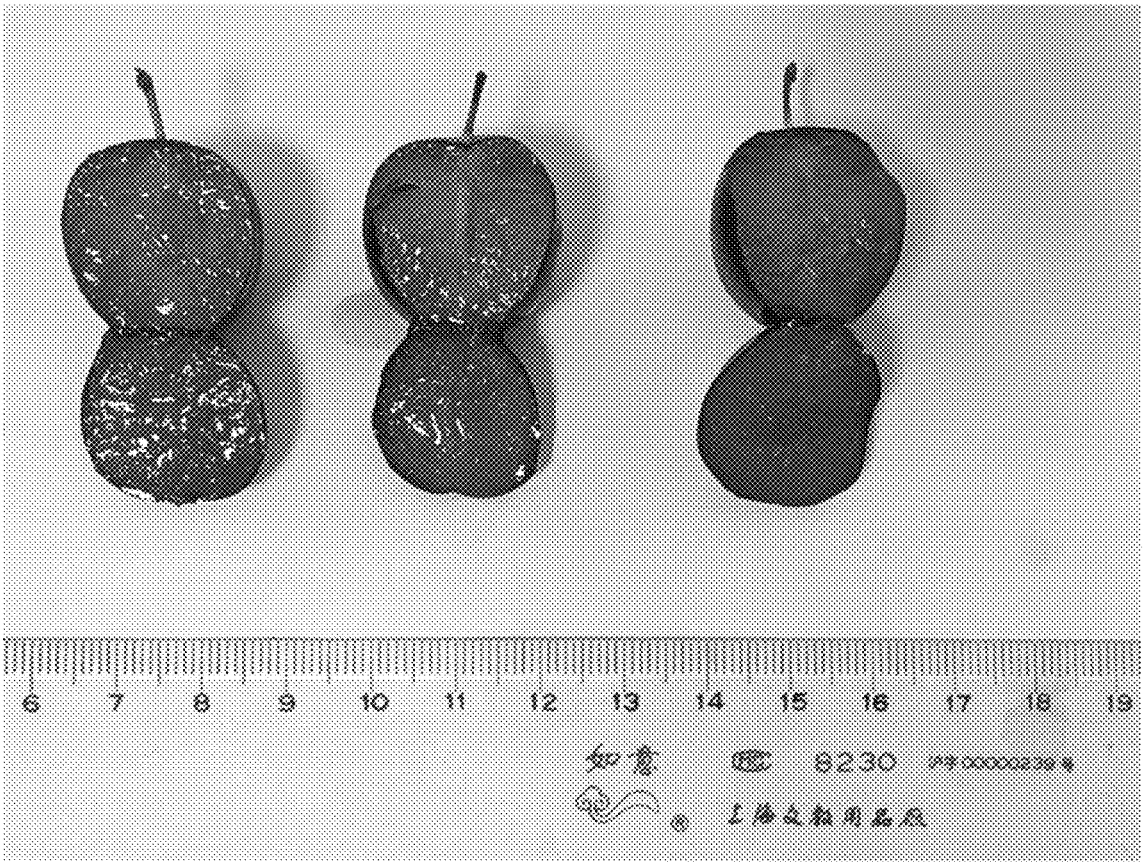
FIG. 4 is the cross-section view of the fruit of the new variety 'Farmer 6-10'.

Throughout this specification, color names beginning with a small letter signify that the name of that color as used in common speech is aptly descriptive. Color names beginning with a capital letter designate values based upon "CMYK International Standard Color Chart", First edition, August 2019. Common color names are also occasionally used.

The descriptive matter which follows pertains to 3-year-old 'Farmer 6-10' trees grown in Qingshuihe Town, Huocheng County, Xinjiang, China, and it is believed to apply to trees of the variety grown under similar conditions of soil and climate elsewhere. The characteristics of 'Farmer 6-10' trees and fruits were observed during the growing season of 2021, continued in 2022. The observed characteristics may vary depending on location and season.

Tree:

General: (Measurements taken on three-year-old trees unless otherwise noted and are based on two-year averages).

*Vigor*.—Medium.
*Posture*.—Open.
*Shape*.—Natural open-center shape.
*Habit*.—Drooping.

Foliage:

*Leaf abscission stage*.—Medium, About October 23$^{rd}$.

Spring shoot: (Data taken in May to June).

*Length of young shoot*.—Medium, approximately 62.73 cm.
*Internode length of young shoot*.—Medium, approximately 1.61 cm.
*Color of young shoot*.—About Reddish Brown.
*Color of tender leaf*.—About Red.
*Shape of leaf blade*.—Rounded.
*Length of leaf blade*.—Short, approximately 5.36 cm.
*Width of leaf blade*.—Approximately 3.66 cm.
*Area of leaf blade*.—Small, approximately 19.68 cm$^2$.
*Color of leaf blade*.—About Green.
*Shape of leaf base*.—Rounded.
*Shape of leaf apex*.—Acuminate.
*Leaf margin teeth*.—Obtusely serrate.
*Length of petiole*.—Medium, approximately 1.31 cm.
*Depth of petiole*.—Medium.
*Pubescence of lower side of petiole*.—Absent.
*Nectary*.—Absent.
*Length/width ratio of leaf blade*.—Small, approximately 1.47:1.
*Glossiness of upper side of leaf blade*.—Medium.
*Pubescence of lower side of blade*.—Absent.

Autumn shoot: (Data taken in September).

*Size of leaf bud*.—Small.
*Shape of leaf bud*.—Oval.
*Bear posture of leaf bud*.—Semi-adnate.
*Size of bud support*.—Small.

Flowers:

*Flower bed on one-year-old shoot*.—Present.
*Pedicel length*.—Approximately 0.95 cm.
*Shape of sepal*.—Medium elliptical.

Initial bloom: (About April 4$^{th}$).

*Posture of sepal*.—Adnate.
*Color of sepal*.—About Brown Green.

Full bloom: (About April 7$^{th}$).

*Diameter of corolla*.—Large, approximately 2.13 cm.
*Shape of petal*.—Rounded.
*Arrangement of petal*.—Adjacent.
*Shape of upper margin of flower*.—Complete.
*Position of stigma in relation to the anthers*.—High.
*Length of petal*.—Approximately 0.94 cm.
*Width of petal*.—Approximately 0.63 cm.

Fruit:

*Time of maturation*.—About July 18$^{th}$.
*Size*.—Very small, approximately 4.25 g.
*Height*.—Approximately 2.15 cm.
*Width*.—Approximately 2.39 cm.
*Shape*.—Rounded.
*Shape base of fruit*.—Flat.
*Lenticels*.—Present, very few and small size.
*Location of maximum transverse diameter of fruit*.—Near middle.
*Shape at apex*.—Rounded and flat.
*Depth of calyx cavity*.—Shallow.
*Width of calyx cavity*.—Narrow.
*Length of fruit stalk*.—Short, approximately 0.97 cm.
*Base of color of skin*.—About Light Yellow C0M60Y90K0.
*Color of fruit skin*.—About Red C0M99Y72K28.
*Thickness of fruit skin*.—Thin.
*Suture line of fruit*.—Shallow.
*Symmetry of fruit*.—Symmetric.
*Color of flesh of fruit*.—About Yellow C0M61Y88K0.
*Firmness of flesh of fruit*.—Soft, approximately 4.74 kg/cm$^2$.
*Juiciness*.—Medium.
*Flesh fiber*.—Many.
*Soluble solids content*.—Very high, approximately 18.72%.
*Fresh-eating quality*.—Medium.

Fruit use: Market use (fresh-eating, processing, and ornamental).

Stone:

*Degree of adherence of stone to flesh*.—Adherent.
*Stone size relative to fruit*.—Large, approximately 9.10%.
*Size*.—Large, approximately 0.39 g.
*Length*.—Approximately 1.32 cm.
*Width*.—Approximately 1.01 cm.
*Shape*.—Oval.
*Symmetry in ventral view, lateral view by length*.—Symmetrical.
*Symmetry in width by length*.—Asymmetrical.
*Position of widest part of stone*.—Near middle.
*Surface of stone*.—Medium, between peach and apricot.
*Surface of stone*.—Medium.
*Width at base of stone*.—Narrow, approximately 0.77 cm.
*State of back of stone*.—Cracked.

What is claimed is:

1. A new and distinct variety of cherry plum tree named 'Farmer 6-10' as herein described and illustrated.

* * * * *